(12) United States Patent
Lenges

(10) Patent No.: US 6,417,364 B1
(45) Date of Patent: Jul. 9, 2002

US006417364B1

(54) POLYMERIZATION OF ETHYLENE

(75) Inventor: Geraldine Marie Lenges, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/995,160

(22) Filed: Nov. 27, 2001

Related U.S. Application Data

(62) Division of application No. 09/564,410, filed on May 2, 2000.
(60) Provisional application No. 60/132,769, filed on May 6, 1999.

(51) Int. Cl.[7] .......................... C07F 9/80; C07D 213/22; C08F 4/44
(52) U.S. Cl. .......................... 546/12; 546/257; 546/258; 526/161; 526/171; 526/172; 502/155; 502/157
(58) Field of Search .................................. 526/101, 171, 526/172; 502/155, 167; 546/12, 257, 258

(56) References Cited

U.S. PATENT DOCUMENTS 6,133,387 A * 10/2000 Xu et al. ..................... 526/172
6,252,022 B1 * 6/2001 Arthur et al. ................ 526/172

* cited by examiner

*Primary Examiner*—David W. Wu
*Assistant Examiner*—R. Harlan

(57) ABSTRACT

Ethylene is polymerized by novel nickel or iron complexes of selected novel 2,2-bipyridine-6-imines, optionally with the addition of other cocatalysts. The polymers are useful for films and molding resins.

9 Claims, No Drawings

POLYMERIZATION OF ETHYLENE

CROSS-REFERENCE TO RELATED APPLICATIONS

This application is a divisional of co-pending application Ser. No. 09/564,410 (filed May 2, 2000), which claims priority under 35 U.S.C. §119 from U.S. Provisional Application Ser. No. 60/132,769 (filed May 6, 1999), which is incorporated by reference herein as if fully set forth.

FIELD OF THE INVENTION

Ethylene is polymerized using selected iron or nickel complexes of 2,2'-bipyridine-6-imines, optionally in the presence of certain activators such alkylaluminum compounds. Also disclosed herein are novel 2,2'-bipyridine-6-imines and their iron and nickel complexes.

TECHNICAL BACKGROUND

Polyethylene is a very important item of commerce, large quantities of various grades of this polymer being produced annually for a large number of uses, such as packaging films and moldings. There are many different methods for making such polyethylenes, including many used commercially, such as free radical polymerization to make low density polyethylene, and many so-called coordination catalysts such as Ziegler-Natta-type and metallocene-type catalysts. Each of these catalyst systems has its advantages and disadvantages, including cost of the polymerization and the particular structure of the polyethylene produced. Due to the importance of polyethylene, new catalyst systems which are economical and/or produce new types of polyethylenes are constantly being sought.

U.S. Pat. No. 5,866,663 describes the polymerization of ethylene and other olefins using nickel and other transition metal complexes of various imines and similar compounds. This publication is incorporated by reference herein for all purposes.

U.S. Pat. No. 5,955,555, WO98/30612, WO98/38228, WO99/02472 and WO99/12981 (all incorporated by reference herein for all purposes) describe the use of iron or cobalt complexes of 2,6-diacylpyridinebisimines or 2,6-pyridinedicarboxaldehydebisimines as catalysts for the polymerization of olefins, mostly of ethylene. These publications describe the preparation of polyethylenes ranging in molecular weight from low molecular weight alpha-olefins and other oligomers to high molecular weight polyethylenes.

EP-A-0454231 (also incorporated by reference herein for all purposes) describes the use of various complexes of transition metals with selected ligands such as "bipyridine" to polymerize ethylene or other olefins.

In all of the publications cited above, the ligands described herein are not mentioned.

SUMMARY OF THE INVENTION

This invention concerns, a first process for the production of polyethylene, comprising the step of contacting, at a temperature of about −100° C. to about +200° C., ethylene and a Ni or Fe complex of a ligand of the formula

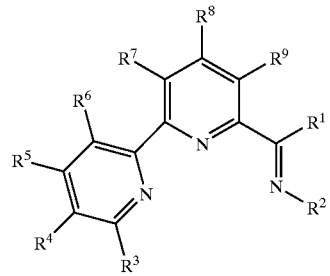

wherein:
R$^1$ is hydrogen, hydrocarbyl or substituted hydrocarbyl;
R$^2$ is hydrocarbyl or substituted hydrocarbyl, provided that a carbon atom of R$^2$ bound to an imino nitrogen atom has at least two carbon atoms bound to it; and
each of R$^3$, R$^4$, R$^5$, R$^6$, R$^7$, R$^8$ and R$^9$ is independently hydrogen, hydrocarbyl, substituted hydrocarbyl or a functional group, provided that any two of R$^3$, R$^4$, R$^5$ R$^6$, R$^7$, R$^8$ and R$^9$ vicinal to one another, or R$^6$ and R$^7$ taken together, may form a ring.

Also disclosed herein is a second process for the production of polyethylene, comprising the step of contacting, at a temperature of about −100° C. to about +200° C., ethylene, a compound of the formula

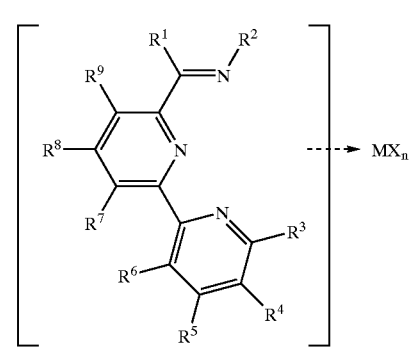

and:
(a) a first compound W, which is a neutral Lewis acid capable of abstracting X$^-$ an alkyl group or a hydride group from M to form WX$^-$, (WR$^{20}$) or WH$^-$, and which is also capable of transferring an alkyl group or a hydride to M, provided that WX$^-$ is a weakly coordinating anion; or
(b) a combination of second compound which is capable of transferring an alkyl or hydride group to M and a third compound which is a neutral Lewis acid which is capable of abstracting X$^-$, a hydride or an alkyl group from M to form a weakly coordinating anion;
wherein:
M is Fe or Ni;
each X is an anion;
n is an integer so that the total number of negative charges on said anion or anions is equal to the oxidation state of M;
R$^1$ is hydrogen, hydrocarbyl or substituted hydrocarbyl;
R$^2$ is hydrocarbyl or substituted hydrocarbyl, provided that a carbon atom of R$^2$ bound to an imino nitrogen atom has at least two carbon atoms bound to it; and each of $R^3$, $R^4$, $R^5$, $R^6$, $R^7$, $R^8$ and $R^9$ is independently hydrogen, hydrocarbyl, substituted hydrocarbyl or a functional group, provided that any two of $R^3$, $R^4$, $R^5$, $R^6$, $R^7$, $R^8$ and $R^9$ vicinal to one another, or $R^6$ and $R^7$ taken together, may form a ring.

This invention also concerns a third process for the production of polyethylene, comprising the step of contacting, at a temperature of about −100° C. to about +200° C., ethylene and a compound of the formula

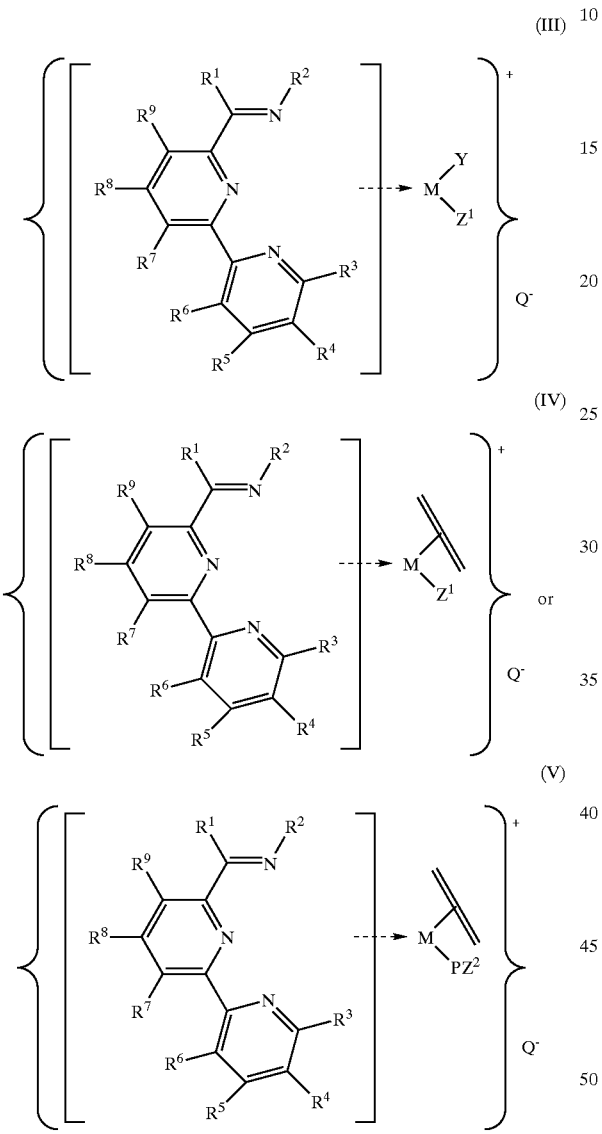

wherein:
- M is Ni or Fe;
- each X is an anion;
- $R^1$ is hydrogen, hydrocarbyl or substituted hydrocarbyl;
- $R^2$ is hydrocarbyl or substituted hydrocarbyl, provided that a carbon atom of $R^2$ bound to an imino nitrogen atom has at least two carbon atoms bound to it;
- each of $R^3$, $R^4$, $R^5$, $R^6$, $R^7$, $R^8$ and $R^9$ is independently hydrogen, hydrocarbyl, substituted hydrocarbyl or a functional group, provided that any two of $R^3$, $R^4$, $R^5$, $R^6$, $R^7$, $R^8$ and $R^9$ vicinal to one another, or $R^6$ and $R^7$ taken together, may form a ring;
- $Z^1$ is hydride or alkyl or an anionic ligand into which ethylene can insert;
- Y is a neutral ligand capable of being displaced by ethylene, or a vacant coordination site;
- Q is a relatively non-coordinating anion;
- P is a divalent polyethylene group containing one or more ethylene units; and
- $Z^2$ is an end group.

Also described herein is a compound of the formula

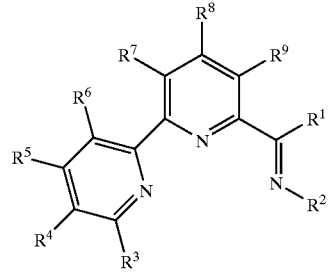

wherein:

$R^1$ is hydrogen, hydrocarbyl or substituted hydrocarbyl;

$R^2$ is hydrocarbyl or substituted hydrocarbyl, provided that a carbon atom of $R^2$ bound to an imino nitrogen atom has at least two carbon atoms bound to it; and each of $R^3$, $R^4$, $R^5$, $R^6$, $R^7$, $R^8$, and $R^9$ is independently hydrogen, hydrocarbyl, substituted hydrocarbyl or a functional group, provided that any two of $R^3$, $R^4$, $R^5$, $R^6$, $R^7$, $R^8$ and $R^9$ vicinal to one another or, $R^6$ and $R^7$ taken together, may form a ring.

Described herein is a compound of the formula

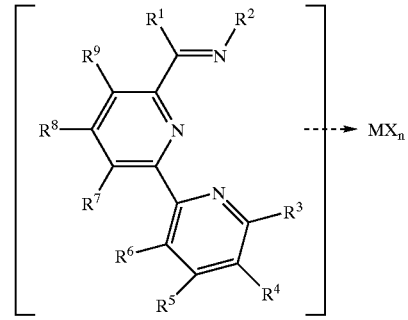

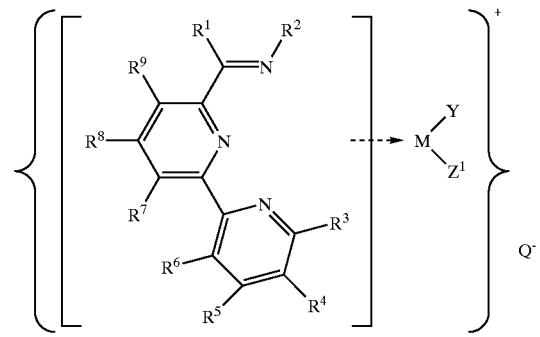

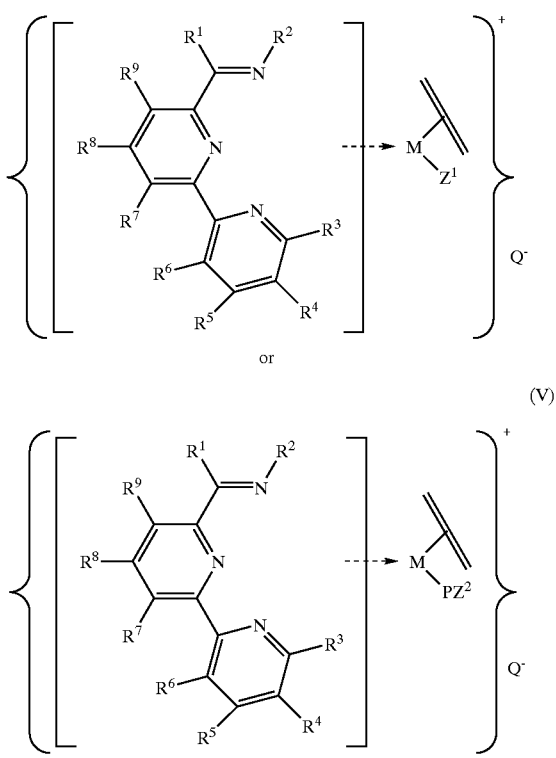

wherein:

M is Fe or Ni;

each X is an anion;

n is an integer so that the total number of negative charges on said anion or anions is equal to the oxidation state of M;

$R^1$ is hydrogen, hydrocarbyl or substituted hydrocarbyl;

$R^2$ is hydrocarbyl or substituted hydrocarbyl, provided that a carbon atom of $R^2$ bound to an imino nitrogen atom has at least two carbon atoms bound to it;

each of $R^3$, $R^4$, $R^5$, $R^6$, $R^7$, $R^8$ and $R^9$ is independently hydrogen, hydrocarbyl, substituted hydrocarbyl or a functional group, provided that any two of $R^3$, $R^4$, $R^5$, $R^6$, $R^7$, $R^8$ and $R^9$ vicinal to one another, or $R^6$ and $R^7$ taken together, may form a ring;

$Z^1$ is hydride or alkyl or an anionic ligand into which ethylene can insert;

Y is a neutral ligand capable of being displaced by ethylene, or a vacant coordination site;

Q is a relatively non-coordinating anion;

P is a divalent polyethylene group containing one or more ethylene units; and $Z^2$ is an end group.

DETAILED DESCRIPTION OF THE PREFERRED EMBODIMENTS

Herein, certain terms are used. Some of them are:

A "hydrocarbyl group" is a univalent group containing only carbon and hydrogen. If not otherwise stated, it is preferred that hydrocarbyl groups herein contain 1 to about 30 carbon atoms.

By "substituted hydrocarbyl" herein is meant a hydrocarbyl group which contains one or more substituent groups which are inert under the process conditions to which the compound containing these groups is subjected. The substituent groups also do not substantially interfere with the process. If not otherwise stated, it is preferred that substituted hydrocarbyl groups herein contain 1 to about 30 carbon atoms. Included in the meaning of "substituted" are heteroaromatic rings.

By "(inert) functional group" herein is meant a group, other than hydrocarbyl or substituted hydrocarbyl, which is inert under the process conditions to which the compound containing the group is subjected. The functional groups also do not substantially interfere with any process described herein that the compound in which they are present may take part in. Examples of functional groups include halo (fluoro, chloro, bromo and iodo), ether such as -$OR^{18}$ wherein $R^{18}$ is hydrocarbyl or substituted hydrocarbyl. In cases in which the functional group may be near a nickel or iron atom, the functional group should not coordinate to the metal atom more strongly than groups in (I) which are shown as coordinating to the metal atom in the complexes, that is they should not displace the desired coordinating group.

By an "alkyl aluminum compound" is meant a compound in which at least one alkyl group is bound to an aluminum atom. Other groups such as alkoxide, hydride and halogen may also be bound to aluminum atoms in the compound.

By "neutral Lewis base" is meant a compound, which is not an ion, that can act as a Lewis base. Examples of such compounds include ethers, amines, sulfides, and organic nitriles.

By "cationic Lewis acid" is meant a cation that can act as a Lewis acid. Examples of such cations are sodium and silver cations.

By "relatively noncoordinating anions" (or "weakly coordinating anions" is meant those anions as are generally referred to in the art in this manner, and the coordinating ability of such anions is known and has been discussed in the literature, see for instance W. Beck., et al., Chem. Rev., vol. 88 p. 1405–1421 (1988), and S. H. Stares, Chem. Rev., vol. 93, p. 927–942 (1993), both of which are hereby included by reference. Among such anions are those formed from the aluminum compounds in the immediately preceding paragraph and $X^-$, including $R^9{}_3AlX^-$, $R^9{}_2AlClX^-$, $R^9AlCl_2X^-$, and "$R^9AlOX^-$", wherein $R^9$ is alkyl. Other useful noncoordinating anions include $BAF^-$ {BAF=tetrakis[3,5-bis(trifluoromethyl)phenyl]borate}, $SbF_6{}^-$, $PF_6{}^-$, and $BF_4{}^-$, trifluoromethanesulfonate, p-toluenesulfonate, $(R_fSO_2)_2N^-$, and $(C_6F_5)_4B^-$.

By an "empty coordination site" is meant a potential coordination site that is not occupied by a ligand. Thus if an ethylene molecule is in the proximity of the empty coordination site, the ethylene molecule may coordinate to the metal atom.

By a "ligand that may add to ethylene" is meant a ligand coordinated to a metal atom into which an ethylene molecule (or a coordinated ethylene molecule) may insert to start or continue a polymerization. For instance, this may take the form of the reaction (wherein L is a ligand):

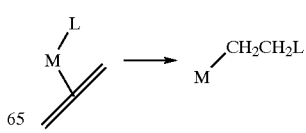

Herein a compound of the "formula"

 (VI)

signifies a ligand L [such as (I)] coordinated to the transition metal group $MX_n$. In this representation whether L is acting as a monodentate, bidentate, tridentate, etc. ligand is unspecified.

In (I) and its various Ni and Fe complexes as described herein it is preferred that:

$R^1$ is hydrogen or hydrocarbyl, more preferably hydrogen or alkyl containing 1 to 10 carbon atoms, especially preferably hydrogen or methyl; and/or $R^2$ is aryl or substituted aryl, more preferably phenyl or substituted phenyl, especially phenyl substituted in the 2, or 2 and 6 positions, with alkyl containing 1 to 10 carbon atoms or halogen, and optionally substituted with alkyl containing 1 to 10 carbon atoms in the 4 position; and/or each of $R^3$, $R^4$, $R^5$, $R^6$, $R^7$, $R^8$ and $R^9$ is hydrogen.

In specific preferred compounds (I) and complexes thereof the following groups are present. In all instances each of $R^3$, $R^4$, $R^5$, $R^6$, $R^7$, $R^8$ and $R^9$ is hydrogen:

$R^1$ is hydrogen and $R^2$ is 2,6-diisopropylphenyl; or
$R^1$ is hydrogen and $R^2$ is 2,4,6-tri-t-butylphenyl; or
$R^1$ is hydrogen and $R^2$ is pentafluorophenyl; or
$R^1$ is methyl and $R^2$ is 2,6-diisopropylphenyl.

(I) may be prepared by the well-known general reaction of a primary amine with a carbonyl compound, in this case a 2,2'-bipyridine-6-carboxaldehyde or a 6-acyl-2,2'-bipyridine, to make an imine. Such preparations are illustrated herein in Examples 1–4.

In (II) it is preferred that X is chloride, bromide or acetylacetonate (acac).

Useful neutral monodentate ligands Y include ethers such as diethyl ether and tetrahydrofuran and nitrites such as acetonitrile.

In the second polymerization process described herein an iron or nickel complex (II) is contacted with ethylene and a neutral Lewis acid W capable of abstracting X⁻, hydride or alkyl from (II) to form a weakly coordinating anion, and must alkylate or be capable of adding a hydride ion to the metal atom, or an additional alkylating agent or an agent capable of adding a hydride anion to the metal atom must be present. The neutral Lewis acid is originally uncharged (i.e., not ionic). Suitable neutral Lewis acids include $SbF_5$, $Ar_3B$ (wherein Ar is aryl) and $BF_3$. Suitable cationic Lewis acids or Bronsted acids include NaBAF, silver trifluoromethanesulfonate, $HBF_4$, or $[C_6H_5N(CH_3)_2]^+$ $[B(C_6F_5)_4]^-$. In those instances in which (II) (and similar catalysts which require the presence of a neutral Lewis acid or a cationic Lewis or Bronsted acid) does not contain an alkyl or hydride group already bonded to the metal atom, the neutral Lewis acid or a cationic Lewis or Bronsted acid also alkylates or adds a hydride to the metal or a separate alkylating or hydriding agent is present, i.e., causes an alkyl group or hydride to become bonded to the metal atom. These alkyl groups, especially methyl, and hydride are groups that may also be $Z^1$ in (III) and (IV).

It is preferred that the alkyl groups in an alkyl aluminum compound contain 1 to 4 carbon atoms each, and more preferred that the alkyl groups are methyl or ethyl.

For instance, alkyl aluminum compounds (see next paragraph) may alkylate (II). However, not all alkyl aluminum compounds may be strong enough Lewis acids to abstract X⁻ or an alkyl group from the metal atom. In that case a separate Lewis acid strong enough to do the abstraction must be present.

A preferred neutral Lewis acid, which can alkylate the metal, is a selected alkyl aluminum compound, such as $R^{19}_3Al$, $R^{19}AlCl_2$, $R^{19}_2AlCl$, and "$R^{19}AlO$" (alkylaluminoxanes), wherein $R^{19}$ is alkyl containing 1 to 25 carbon atoms, preferably 1 to 4 carbon atoms. Suitable alkyl aluminum compounds include methylaluminoxane (which is an oligomer with the general formula $[MeAlO]_n$), $(C_2H_5)_2AlCl$, $C_2H_5AlCl_2$ and $[(CH_3)_2CHCH_2]_3Al$.

Metal hydrides such as $NaBH_4$ may be used to bond hydride groups to the metal M.

In the third polymerization process described herein a nickel or iron complex of (I) is either added to the polymerization process or formed in situ in the process. In fact, more than one such complex may be formed during the course of the process, for instance formation of an initial complex and then reaction of that complex to form a living ended polymer containing such a complex.

Examples of such complexes which may be formed initially in situ include (III) and (IV), as defined above, and wherein the "parallel lines" are an ethylene molecule coordinated to the metal. These complexes may be added directly to the process or formed in situ. For instance, (III) may be formed by the reaction of (II) with a neutral Lewis acid such as an alkyl aluminum compound. Another method of forming such a complex in situ is adding a suitable iron or nickel compound such nickel [II] acetylacetonate, (I) and an alkyl aluminum compound. Other metal salts in which anions similar to acetylacetonate are present, and which may be removed by reaction with the Lewis or Bronsted acid. For instance metal halides and carboxylates (such as acetates) may be used, particularly if they are slightly soluble in the process medium. It is preferred that these precursor metal salts be at least somewhat soluble in the process medium.

After the ethylene polymerization has started, the complex may be in a form such as (V) as defined above wherein P may be a divalent (poly)ethylene group of the formula $-(CH_2CH_2)_x-$ wherein x is an integer of 1 or more, and $Z^2$ is an end group (assuming no branching taking place during polymerization), for example the groups listed for $Z^1$ above. Those skilled in the art will note that (V) is in essence a polymer containing a so-called living end. It is preferred that M be in +2 oxidation state in (III), (IV) and (V). Compounds such as (III), (IV) and (V) may or may not be stable away from an environment similar to that of the polymerization process, but they may be detected by NMR spectroscopy, particularly one or both of $^1H$ and $^{13}C$ NMR, and particularly at lower temperatures. Such techniques, especially for polymerization "intermediates" of these types are known, see for instance U.S. Pat. No. 5,880,241, especially Examples 197–203, which is hereby included by reference.

(III), (IV) and (V) may also be used in the absence of any "co-catalysts" or "activators" to polymerize ethylene in a third polymerization process. Except for the ingredients in the process, the process conditions for the third process, such as temperature pressure, polymerization medium, etc., may be the same as for the first and second polymerization processes, and preferred conditions for those processes are also preferred for the third polymerization process.

In all the polymerization processes herein, the temperature at which the polymerization is carried out is about −100° C. to about +200° C., preferably about 0° C. to about 150° C., more preferably about 25° C. to about 100° C. A convenient ethylene pressure to use in the polymerization is about 300 kPa to about 275 MPa, more preferably about 2 MPa to about 100 MPa.

The polymerization processes herein may be run in the presence of various liquids, particularly aprotic organic liquids. The catalyst system, ethylene, and polyethylene may be soluble or insoluble in these liquids, but obviously these liquids should not prevent the polymerization from occurring. Suitable liquids include alkanes, cycloalkanes, selected halogenated hydrocarbons, and aromatic hydrocarbons. Hydrocarbons are the preferred solvent. Specific useful solvents include hexane, toluene, benzene, chloroform, methylene chloride, 1,2,4-trichlorobenzene, p-xylene, and cyclohexane.

The catalysts herein may be "heterogenized" by coating or otherwise attaching them to solid supports, such as silica or alumina. Where an active catalyst species is formed by reaction with a compound such as an alkylaluminum compound, a support on which the alkylaluminum compound is first coated or otherwise attached is contacted with the nickel compound precursor to form a catalyst system in which the active nickel catalyst is "attached" to the solid support. These supported catalysts may be used in polymerizations in organic liquids, as described in the immediately preceding paragraph. They may also be used in so-called gas phase polymerizations in which the olefin(s) being polymerized are added to the polymerization as gases and no liquid supporting phase is present.

It is known that certain transition metal containing polymerization catalysts including those disclosed herein, are especially useful in varying the branching in polyolefins made with them, see for instance previously incorporated U.S. Pat. Nos. 5,714,556, 5,880,241, WO98/30610 and WO99/30609. It is also known that blends of distinct polymers, that vary for instance in the properties listed above, may have advantageous properties compared to "single" polymers. For instance it is known that polymers with broad or bimodal molecular weight distributions may be melt processed (be shaped) more easily than narrower molecular weight distribution polymers. Similarly, thermoplastics such as crystalline polymers may often be toughened by blending with elastomeric polymers.

Therefore, methods of producing polymers which inherently produce polymer blends are useful especially if a later separate (and expensive) polymer mixing step can be avoided. However in such polymerizations one should be aware that two different catalysts may interfere with one another, or interact in such a way as to give a single polymer.

In such a process the catalysts disclosed herein can be termed the first active polymerization catalyst. Monomers useful with these catalysts are those described (and also preferred) above.

A second active polymerization catalyst (and optionally one or more others) is used in conjunction with the first active polymerization catalyst. The second active polymerization catalyst may be another late transition metal catalyst, for example as described in previously incorporated U.S. Pat. Nos. 5,714,556, 5,880,241, 5,955,555, WO98/30610 and 98/30609. Other useful types of catalysts may also be used for the second active polymerization catalyst. For instance so-called Ziegler-Natta and/or metallocene-type catalysts may also be used. These types of catalysts are well known in the polyolefin field, see for instance *Angew. Chem., Int. Ed. Engl.*, vol. 34, p. 1143–1170 (1995), EP-A-0416815 and U.S. Pat. No. 5,198,401 for information about metallocene-type catalysts, and J. Boor Jr., *Ziegler-Natta Catalysts and Polymerizations*, Academic Press, New York, 1979 for information about Ziegler-Natta-type catalysts, all of which are hereby included by reference. Many of the useful polymerization conditions for all of these types of catalysts and the first active polymerization catalysts coincide, so conditions for the polymerizations with first and second active polymerization catalysts are easily accessible. Oftentimes the "co-catalyst" or "activator" is needed for metallocene or Ziegler-Natta-type polymerizations. In many instances the same compound, such as an alkylaluminum compound, may be used as an "activator" for some or all of these various polymerization catalysts.

Suitable catalysts for the second polymerization catalyst also include metallocene-type catalysts, as described in U.S. Pat. No. 5,324,800 and EP-A-0129368; particularly advantageous are bridged bis-indenyl metallocenes, for instance as described in U.S. Pat. No. 5,145,819 and EP-A-0485823. Another class of suitable catalysts comprises the well-known constrained geometry catalysts, as described in EP-A-0416815, EP-A-0420436, WP-A-0671404, EP-A-0643066 and WO91/04257. Also the class of transition metal complexes described in WO96/13529 can be used.

In one preferred process described herein the first olefin(s) [ethylene polymerized by the first active polymerization catalyst] and second olefin(s) [the monomer(s) polymerized by the second active polymerization catalyst] are identical, and preferred olefins in such a process are the same as described immediately above. The second olefins may also be a single olefin or a mixture of olefins to make a copolymer. Again it is preferred that they be identical particularly in a process in which polymerization by the first and second active polymerization catalysts make polymer simultaneously.

In some processes herein the first active polymerization catalyst may polymerize a monomer that may not be polymerized by said second active polymerization catalyst, and/or vice versa. In that instance two chemically distinct polymers may be produced. In another scenario two monomers would be present, with one polymerization catalyst producing a copolymer, and the other polymerization catalyst producing a homopolymer, or two copolymers may be produced which vary in the molar proportion or repeat units from the various monomers. Other analogous combinations will be evident to the artisan.

In another variation of this process one of the polymerization catalysts makes an oligomer of an olefin, preferably ethylene, which oligomer has the formula $R^{70}CH=CH_2$, wherein $R^{70}$ is n-alkyl, preferably with an even number of carbon atoms. The other polymerization catalyst in the process then (co)polymerizes this olefin, either by itself or preferably with at least one other olefin, preferably ethylene, to form a branched polyethylene. Preparation of the oligomer (which is sometimes called an α-olefin) by a second active polymerization-type of catalyst can be found in previously incorporated U.S. Pat. No. 5,880,241, and WO99/02472 (also incorporated by reference herein for all purposes).

Likewise, conditions for such polymerizations, using catalysts of the second active polymerization type, will also be found in the appropriate above mentioned references.

Two chemically different active polymerization catalysts are used in this polymerization process. The first active polymerization catalyst is described in detail above. The second active polymerization catalyst may also meet the limitations of the first active polymerization catalyst, but must be chemically distinct. For instance, it may have a different transition metal present, and/or utilize a different type of ligand and/or the same type of ligand which differs in structure between the first and second active polymerization catalysts. In one preferred process, the ligand type and the metal are the same, but the ligands differ in their substituents.

Included within the definition of two active polymerization catalysts are systems in which a single polymerization catalyst is added together with another ligand, preferably the same type of ligand, which can displace the original ligand coordinated to the metal of the original active polymerization catalyst, to produce in situ two different polymerization catalysts.

The molar ratio of the first active polymerization catalyst to the second active polymerization catalyst used will depend on the ratio of polymer from each catalyst desired, and the relative rate of polymerization of each catalyst under the process conditions. For instance, if one wanted to prepare a "toughened" thermoplastic polyethylene that contained 80% crystalline polyethylene and 20% rubbery polyethylene, and the rates of polymerization of the two catalysts were equal, then one would use a 4:1 molar ratio of the catalyst that gave crystalline polyethylene to the catalyst that gave rubbery polyethylene. More than two active polymerization catalysts may also be used if the desired product is to contain more than two different types of polymer.

The polymers made by the first active polymerization catalyst and the second active polymerization catalyst may be made in sequence, i.e., a polymerization with one (either first or second) of the catalysts followed by a polymerization with the other catalyst, as by using two polymerization vessels in series. However it is preferred to carry out the polymerization using the first and second active polymerization catalysts in the same vessel(s), i.e., simultaneously. This is possible because in most instances the first and second active polymerization catalysts are compatible with each other, and they produce their distinctive polymers in the other catalyst's presence. Any of the processes applicable to the individual catalysts may be used in this polymerization process with 2 or more catalysts, i.e., gas phase, liquid phase, continuous, etc.

The polymers produced by this "mixed catalyst" process may vary in molecular weight and/or molecular weight distribution and/or melting point and/or level of crystallinity, and/or glass transition temperature and/or other factors. For copolymers the polymers may differ in ratios of comonomers if the different polymerization catalysts polymerize the monomers present at different relative rates. The polymers produced are useful as molding and extrusion resins and in films as for packaging. They may have advantages such as improved melt processing, toughness and improved low temperature properties.

Hydrogen may be used to lower the molecular weight of polyethylene produced in the first or second processes. It is preferred that the amount of hydrogen present be about 0.01 to about 50 mole percent of the ethylene present, preferably about 1 to about 20 mole percent. The relative concentrations of hydrogen and ethylene may be regulated by their partial pressures.

Included herein within the definitions of all the polymerization processes are mixtures of starting materials that lead to the formation in situ of the transition metal compounds specified in all of the polymerization processes.

In the Examples, various abbreviations are used:
acac—acetylacetonate
DME—1,2-dimethoxyethane
DSC—Differential Scanning calorimetry
GPC—Gel Permeation Chromatography
Mn—number average molecular weight
Mw—weight average molecular weight
PE—polyethylene
PMAO—methylaluminoxane Melting point was determined by DSC at a heating rate of 10° C./min. The melting point was taken as the peak of the melting endotherm on the second heat. Usually the DSCs of these polymers exhibited broad melting endotherms.

EXAMPLES 1–5

Preparation of Ligands (I)

This procedure illustrates the synthesis of the 2,2'-bipyridinephenylimine ligands. A 100 mL round-bottomed flask was charged with 1.0 g (5.43 mmol) of 2,2'-bipyridine-6-carboxaldehyde. Anhydrous methanol (50 mL) was added forming an orange solution. 2,6-Diisopropylaniline (0.96 g, 5.43 mmol) and 3 drops of formic acid were added and the reaction was stirred overnight. A yellow precipitate began forming after approximately 15 min. The reaction mixture was filtered and the product was washed with methanol and dried in vacuo. A yellow solid (1.22 g, 65%), (I–1), was recovered. $^1$H NMR (300 MHz, 20° C., CDCl$_3$) δ8.69–7.12 (m, 10H, bipyridine and aromatic protons); 8.39 (s, 1H, backbone H); 2.99 (septet, 2H, CH(CH$_3$)$_2$); 1.18 (d, 12H, CH(CH$_3$)$_2$).

Structures of the various ligands (I) are given in Table 1. In all instances $R^3$, $R^4$, $R^5$, $R^6$, R , $R^8$ and ere hydrogen.

TABLE 1

| Example | Ligand | $R^1$ | $R^2$ |
|---|---|---|---|
| 1 | (I-1) | H | 2,6-diisopropylphenyl |
| 2 | (I-2) | H | 2,4,6-tri-t-butylphenyl |
| 3 | (I-3) | H | pentafluorophenyl |
| 4 | (I-4) | CH$_3$ | 2,6-diisopropylphenyl |
| 5 | (I-5) | CH$_3$ | pentafluorophenyl |

EXAMPLES 6–15

Preparation of Fe and Ni Complexes

This is a general procedure for the synthesis of NiBr$_2$ complexes of 2,2'-bipyridinephenylimines. In a drybox, a round bottom flask was charged with (DME)NiBr$_2$ (0.225 g, 0.728 mmol). Dichloromethane (10 mL) was added forming a peach suspension. 2,2'-Bipyridinephenylimine (0.728 mmol) was added and the resulting solution was stirred 12 h. The reaction mixture was filtered (sometimes through Celite®) and the solvent was removed in vacuo. The product was washed with pentane and dried in vacuo.

This is a general procedure for the synthesis of Ni(acac)$_2$ complexes of 2,2'-bipyridinephenylimines. In a drybox, a round bottom flask was charged with Ni(acac)$_2$ (0.100 g, 0.28 mmol). Tetrahydrofuran (30 mL) was added forming a green suspension. 2,2'-Bipyridinephenylimine (0.728 mmol) was added and the resulting solution was stirred 12 h. The reaction mixture was filtered through Celite® and the solvent was removed in vacuo. The product was washed with pentane and dried in vacuo.

This is a general procedure for the synthesis of FeCl$_2$ complexes of 2,2'-bipyridinephenylimines. In a drybox, a round bottom flask was charged with 2,2'-bipyridinephenylimine (0.58 mmol). Tetrahydrofuran (30 mL) was added forming a yellow solution. FeCl$_2$ (0.074 g, 0.58 mmol) was added and the resulting suspension was stirred 12 h. The reaction mixture was filtered and the product was washed with tetrahydrofuran and pentane and dried in vacuo.

For each of the complexes made, yields and other data are given in Table 2.

TABLE 2

| Example | Ligand | Metal Compound | Yield g (%) | Color |
|---|---|---|---|---|
| 6 | (I-1) | NiBr$_2$ | 0.25 (61) | brown |
| 7 | (I-2) | NiBr$_2$ | 0.23 (75) | orange |
| 8 | (I-3) | NiBr$_2$ | - (75) | royal blue |
| 9 | (I-4) | NiBr$_2$ | 0.20 (50) | dark green |
| 10 | (I-3) | Ni(acac)$_2$ | 0.083 (50) | forest green |
| 11 | (I-5) | Ni(acac)$_2$ | 0.089 (52) | pale green |
| 12 | (I-1) | FeCl$_2$ | 0.14 (50) | royal blue |
| 13 | (I-3) | FeCl$_2$ | 0.20 (70) | royal blue |
| 14 | (I-4) | FeCl$_2$ | 0.17 (64) | royal blue |
| 15 | (I-2) | FeCl$_2$ | - (75) | orange |

EXAMPLES 16–23

Polymerizations with Ethylene

This procedure is general for ethylene polymerization. A reactor was charged with Ni or Fe complex (0.03 mmol). 1,2,4-Trichlorobenzene (3 mL) was added and the catalyst solution was placed in a −20° C. freezer for 15 min. Another layer of 1,2,4-trichlorobenzene (3 mL) was added and the reactor was again placed in a −20° C. freezer for 15 min. This procedure separated the catalyst solution from the co-catalyst through a layer of frozen solvent. PMAO co-catalyst (1 mL) was added and the frozen reactor was brought of the drybox. The reactor was evacuated, charged with ethylene to 6.9 MPa (1000 psi) and the polymerization run for 16 h. Polyethylene was recovered by precipitation in methanol, washed with 6 M HCl and methanoland dried under high vacuum overnight. Details of the various polymerizations are given in Table 3. By DSC, in Example 16 the Mn was 540 and the Mw was 2569, and in Example 21 the Mn was 1676 and the Mw was 80,000.

TABLE 3

| Example | Complex of Example | Yield PE mg | Tm, ° C. |
|---|---|---|---|
| 16 | 11 | 1200 | 121 |
| 17 | 14 | 380 | 121 |
| 18 | 12 | 30 | 124 |
| 19 | 13 | 50 | 121 |
| 20 | 5 | 70 | 121 |
| 21 | 6 | 140 | 128 |
| 22 | 8 | 20 | 129 |
| 23 | 10 | 100 | 130 |

What is claimed is:

1. A compound of the formula

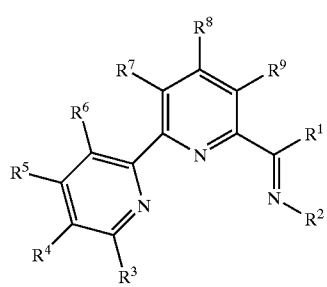

(I)

wherein:

R$^1$ is hydrogen, hydrocarbyl or substituted hydrocarbyl;

R$^2$ is hydrocarbyl or substituted hydrocarbyl, provided that a carbon atom of R$^2$ bound to an imino nitrogen atom has at least two carbon atoms bound to it; and each of R$^3$, R$^4$, R$^5$, R$^6$, R$^7$, R$^8$ and R$^9$ is independently hydrogen, hydrocarbyl, substituted hydrocarbyl or a functional group, provided that any two of R$^3$, R$^4$, R$^5$, R$^6$, R$^7$, R$^8$ and R$^9$ vicinal to one another, or R$^6$ and R$^7$ taken together, may form a ring.

2. The compound as recited in claim 1, wherein R$^1$ is hydrogen or alkyl containing 1 to 10 carbon atoms, and each of R$^3$, R$^4$, R$^5$, R$^6$, R$^7$, R$^8$ and R$^9$ is hydrogen.

3. The compound as recited in claim 1, wherein R$^2$ is aryl or substituted aryl.

4. The compound as recited in claim 2, wherein R$^2$ is phenyl or substituted phenyl.

5. A compound of the formula

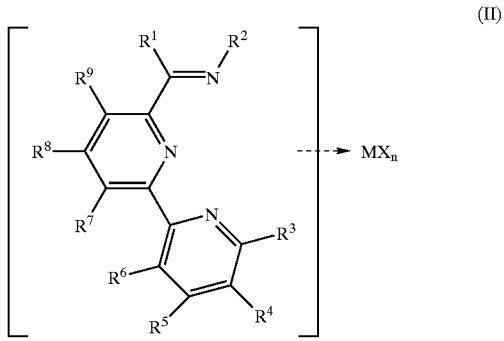

(II)

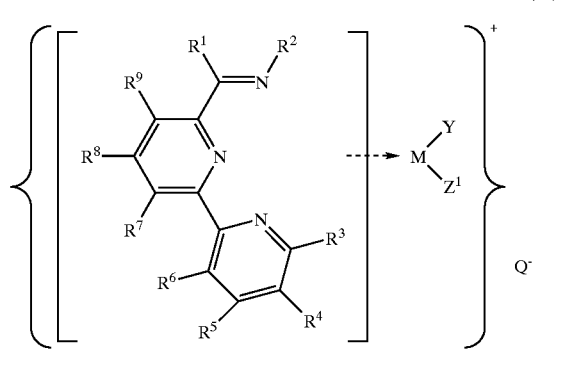

(III)

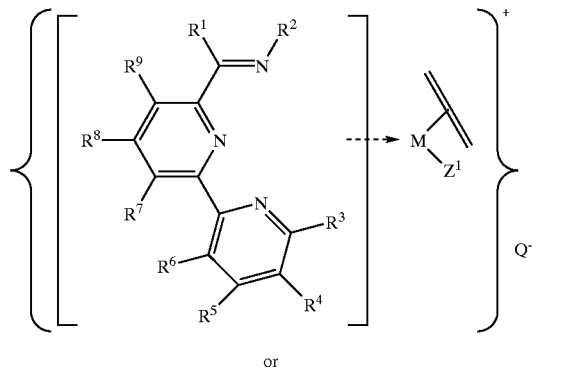

(IV)

or

-continued

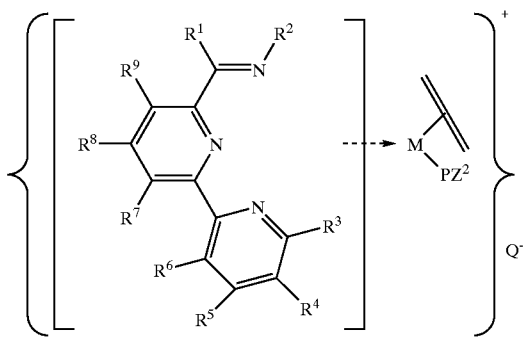

(V)

wherein:

M is Fe or Ni;

each X is an anion;

n is an integer so that the total number of negative charges on said anion or anions is equal to the oxidation state of M;

$R^1$ is hydrogen, hydrocarbyl or substituted hydrocarbyl;

$R^2$ is hydrocarbyl or substituted hydrocarbyl, provided that a carbon atom of $R^2$ bound to an imino nitrogen atom has at least two carbon atoms bound to it;

each of $R^3$, $R^4$, $R^5$, $R^6$, $R^7$, $R^8$ and $R^9$ is independently hydrogen, hydrocarbyl, substituted hydrocarbyl or a functional group, provided that any two of $R^3$, $R^4$, $R^5$, $R^6$, $R^7$, $R^8$ and $R^9$ vicinal to one another or $R^6$ and $R^7$ taken together may form a ring;

$Z^1$ is hydride or alkyl or any other anionic ligand into which ethylene can insert;

Y is a neutral ligand capable of being displaced by ethylene or a vacant coordination site;

Q is a relatively non-coordinating anion;

P is a divalent polyethylene group containing one or more ethylene molecules; and $Z^2$ is an end group.

6. The compound as recited in claim 5, wherein $R^1$ is hydrogen or alkyl containing 1 to 10 carbon atoms, and each of $R^3$, $R^4$, $R^5$, $R^6$, $R^7$, $R^8$ and $R^9$ is hydrogen.

7. The compound as recited in claim 5, wherein $R^2$ is aryl or substituted aryl.

8. The compound as recited in claim 6, wherein $R^2$ is phenyl or substituted phenyl.

9. An olefin polymerization catalyst comprising the compound of claim 5.

* * * * *